US006033100A

United States Patent [19]
Marquiss et al.

[11] Patent Number: 6,033,100
[45] Date of Patent: Mar. 7, 2000

[54] FLOATING HEAD ASSEMBLY

[75] Inventors: Samuel A. Marquiss, Santa Clara; Glenn R. Edwards; Douglas N. Modlin, both of Palo Alto, all of Calif.

[73] Assignee: LJL BioSystems, Inc., Sunnyvale, Calif.

[21] Appl. No.: 09/118,310

[22] Filed: Jul. 16, 1998

Related U.S. Application Data

[63] Continuation of application No. 09/062,472, Apr. 17, 1998, and a continuation of application No. PCT/US98/14575, Jul. 15, 1998

[60] Provisional application No. 60/052,876, Jul. 16, 1998, provisional application No. 60/059,639, Sep. 20, 1997, provisional application No. 60/063,811, Oct. 31, 1997, provisional application No. 60/072,499, Jan. 26, 1998, provisional application No. 60/072,780, Jan. 27, 1998, provisional application No. 60/075,414, Feb. 20, 1998, provisional application No. 60/075,806, Feb. 24, 1998, provisional application No. 60/082,253, Apr. 17, 1998, provisional application No. 60/084,167, May 4, 1998, provisional application No. 60/085,335, May 13, 1998, provisional application No. 60/085,500, May 14, 1998, and provisional application No. 60/089,848, Jun. 19, 1998.

[51] Int. Cl.⁷ .................................................. F21V 21/18
[52] U.S. Cl. ............................ 362/581; 362/288; 385/90
[58] Field of Search ................................ 385/53, 58, 60, 385/70, 72, 76–78, 88, 90, 92, 16, 19, 22, 25; 362/267, 288, 366, 455, 551, 581, 369, 390

[56] References Cited

U.S. PATENT DOCUMENTS

| | | | |
|---|---|---|---|
| 2,719,214 | 9/1955 | Potter | 362/267 |
| 3,013,467 | 12/1961 | Minsky | 356/432 |
| 3,423,581 | 1/1969 | Baer | 362/551 |
| 3,516,736 | 6/1970 | Weaver | 359/823 |
| 3,849,654 | 11/1974 | Malvin | 250/363 |
| 3,932,023 | 1/1976 | Humer | 385/88 |
| 4,011,451 | 3/1977 | Nelson | 250/343 |
| 4,067,653 | 1/1978 | Fletcher et al. | 356/204 |
| 4,076,420 | 2/1978 | De Maeyer et al. | 356/73 |
| 4,100,416 | 7/1978 | Hirschfeld | 250/461 |
| 4,144,452 | 3/1979 | Harte | 250/302 |
| 4,150,870 | 4/1979 | D'Auria | 385/25 |
| 4,203,670 | 5/1980 | Bromberg | 356/367 |
| 4,341,957 | 7/1982 | Wieder | 250/461.2 |
| 4,451,149 | 5/1984 | Noeller | 356/317 |
| 4,485,430 | 11/1984 | Fustel | 362/267 |
| 4,501,970 | 2/1985 | Nelson | 250/458.1 |
| 4,567,847 | 2/1986 | Linner | 118/50.1 |
| 4,626,684 | 12/1986 | Landa | 250/328 |
| 4,685,801 | 8/1987 | Minekane | 356/328 |
| 4,699,512 | 10/1987 | Koshi | 356/318 |
| 4,704,255 | 11/1987 | Jolley | 422/101 |
| 4,707,067 | 11/1987 | Haberland et al. | 385/90 |
| 4,724,217 | 2/1988 | Miller | 436/82 |
| 4,730,921 | 3/1988 | Klein et al. | 356/39 |
| 4,738,825 | 4/1988 | Kelln et al. | 422/72 |
| 4,741,619 | 5/1988 | Humphries | 356/246 |
| 4,753,501 | 6/1988 | Battle | 385/22 |
| 4,762,420 | 8/1988 | Bowley | 356/436 |
| 4,772,453 | 9/1988 | Lisenbee | 422/52 |
| 4,784,275 | 11/1988 | Fridge | 209/558 |
| 4,810,096 | 3/1989 | Russell et al. | 356/436 |
| 4,826,660 | 5/1989 | Smith et al. | 422/68 |
| 4,855,930 | 8/1989 | Chao et al. | 364/497 |
| 4,868,103 | 9/1989 | Stavrianopoulos et al. | 435/5 |
| 4,873,633 | 10/1989 | Mezei et al. | 356/39 |
| 4,877,965 | 10/1989 | Dandliker et al. | 250/458.1 |
| 4,885,087 | 12/1989 | Kopf | 200/321.72 |
| 4,892,409 | 1/1990 | Smith | 356/414 |
| 4,923,819 | 5/1990 | Fernandez et al. | 436/518 |
| 4,936,682 | 6/1990 | Hoyt | 356/414 |
| 4,948,442 | 8/1990 | Manns | 156/73.1 |
| 4,968,148 | 11/1990 | Chow et al. | 356/427 |
| 4,979,821 | 12/1990 | Schutt et al. | 356/246 |
| 5,009,488 | 4/1991 | Fay et al. | 359/889 |
| 5,039,219 | 8/1991 | James et al. | 356/318 |
| 5,047,215 | 9/1991 | Manns | 422/101 |
| 5,058,045 | 10/1991 | Ma | 364/708 |
| 5,082,628 | 1/1992 | Andreotti et al. | 422/82.08 |
| 5,084,246 | 1/1992 | Lyman et al. | 422/101 |
| 5,091,652 | 2/1992 | Mathies et al. | 250/458.1 |
| 5,095,517 | 3/1992 | Monguzzi et al. | 385/90 |
| 5,096,807 | 3/1992 | Leaback | 435/6 |
| 5,169,601 | 12/1992 | Ohta et al. | 422/73 |
| 5,192,510 | 3/1993 | Zoha et al. | 422/82.05 |
| 5,206,568 | 4/1993 | Bjornson et al. | 318/568.1 |
| 5,208,161 | 5/1993 | Saunders et al. | 356/346 |
| 5,208,651 | 5/1993 | Buican | 356/346 |
| 5,225,164 | 7/1993 | Astle | 422/102 |

| | | | |
|---|---|---|---|
| 5,257,202 | 10/1993 | Feddersen et al. | 364/498 |
| 5,270,788 | 12/1993 | Cercek et al. | 356/318 |
| 5,273,718 | 12/1993 | Sköld et al. | 422/101 |
| 5,275,951 | 1/1994 | Chow et al. | 436/50 |
| 5,315,015 | 5/1994 | Hui et al. | 549/223 |
| 5,317,485 | 5/1994 | Merjanian | 362/581 |
| 5,319,436 | 6/1994 | Manns et al. | 356/246 |
| 5,323,008 | 6/1994 | Studholme et al. | 250/458.1 |
| 5,340,716 | 8/1994 | Ullman et al. | 435/6 |
| 5,340,747 | 8/1994 | Eden | 436/172 |
| 5,355,215 | 10/1994 | Schroeder et al. | 356/317 |
| 5,361,626 | 11/1994 | Colligan et al. | 73/40.7 |
| 5,384,093 | 1/1995 | Ootani et al. | 422/63 |
| 5,401,465 | 3/1995 | Smethers et al. | 422/52 |
| 5,418,371 | 5/1995 | Aslund et al. | 250/458.1 |
| 5,420,408 | 5/1995 | Weyrauch et al. | 235/454 |
| 5,436,718 | 7/1995 | Fernandes et al. | 356/73 |
| 5,445,935 | 8/1995 | Royer | 435/6 |
| 5,449,921 | 9/1995 | Baba | 250/583 |
| 5,457,527 | 10/1995 | Manns et al. | 356/246 |
| 5,459,300 | 10/1995 | Kasman | 219/433 |
| 5,480,804 | 1/1996 | Niwa et al. | 435/286.1 |
| 5,485,530 | 1/1996 | Lakowicz et al. | 382/191 |
| 5,487,872 | 1/1996 | Hafeman et al. | 422/102 |
| 5,491,343 | 2/1996 | Brooker | 250/458.1 |
| 5,512,492 | 4/1996 | Herron et al. | 436/518 |
| 5,528,046 | 6/1996 | Ishikawa | 250/461.2 |
| 5,537,343 | 7/1996 | Kikinis et al. | 364/708.1 |
| 5,542,012 | 7/1996 | Fernandes et al. | 385/25 |
| 5,557,398 | 9/1996 | Wechsler et al. | 356/318 |
| 5,589,136 | 12/1996 | Northrup et al. | 422/102 |
| 5,589,350 | 12/1996 | Bochner | 435/29 |
| 5,589,351 | 12/1996 | Harootunian | 435/29 |
| 5,592,289 | 1/1997 | Norris | 356/244 |
| 5,593,867 | 1/1997 | Walker et al. | 435/91.2 |
| 5,595,710 | 1/1997 | Van Dusen et al. | 422/104 |
| 5,599,500 | 2/1997 | Jones | 422/62 |
| 5,604,130 | 2/1997 | Warner et al. | 435/286.7 |
| 5,620,894 | 4/1997 | Barger et al. | 435/286.2 |
| 5,626,134 | 5/1997 | Zuckerman | 128/633 |
| 5,631,734 | 5/1997 | Stern et al. | 356/317 |
| 5,633,724 | 5/1997 | King et al. | 356/445 |
| 5,635,402 | 6/1997 | Alfano et al. | 436/63 |
| 5,641,633 | 6/1997 | Linn et al. | 435/6 |
| 5,663,545 | 9/1997 | Marquiss | 235/375 |
| 5,676,943 | 10/1997 | Baetge et al. | 424/93.21 |
| 5,679,310 | 10/1997 | Manns | 422/102 |
| 5,736,410 | 4/1998 | Zarling et al. | 436/172 |
| 5,780,857 | 7/1998 | Harju et al. | 250/458.1 |
| 5,825,617 | 10/1998 | Kochis et al. | 361/686 |
| 5,842,582 | 12/1998 | DeStefano, Jr. | 211/60.1 |

FOREIGN PATENT DOCUMENTS

| | | |
|---|---|---|
| 0 266 881 A2 | 5/1988 | European Pat. Off. . |
| 2 215 838 | 9/1989 | United Kingdom . |
| 2 228 081 | 8/1990 | United Kingdom . |

OTHER PUBLICATIONS

*Fundamentals of Light Microscopy*, Spencer, Cambridge University Press, 1982.

Basic Fluorescence Microscopy, Taylor et al., *Methods in Cell Biology*, vol. 29, pp. 207–237, 1989.

Quantitative Fluorescence Microscopy Using Photomultiplier Tubes and Imaging Detectors, Wampler et al., *Methods in Cell Biology*, vol. 29, pp. 239–267, 1989.

Three–Dimensional Confocal Fluorescence Microscopy, Brakenhoff et al., *Methods in Cell Biology*, vol. 30, pp. 379–389, 1989.

Laser Scanning Confocal Microscopy of Living Cells, Lemasters et al., *Optical Microscopy: Emerging Methods and Applications*, pp. 339–345, 1993.

Time–Resolved Fluorescence Lifetime Imaging, vande Ven et al., *Optical Microscopy: Emerging Methods and Applications*, pp. 373–389, 1993.

*Primary Examiner*—Alan Cariaso
*Attorney, Agent, or Firm*—Kolisch, Hartwell, Dickinson, McCormack & Heuser

[57] ABSTRACT

Devices and methods for transmitting light through an aperture in a surface substantially without leakage. In one embodiment, the device comprises an optical relay structure having an end configured to transmit light, and an opaque collar positioned around the end and configured to reorient to conform to the surface when the end and the aperture are aligned. In another embodiment, the device comprises an optical relay structure having an end configured to transmit light, and an opaque collar positioned around the end and spring-biased relative to the end, so that the opaque collar is forced against the surface when the end and the aperture are aligned. The devices further may include a stop mechanism for limiting movement of the opaque collar, a registration mechanism for aligning the end and the aperture, and a light source and/or a detector for generating or detecting light, among others.

42 Claims, 6 Drawing Sheets

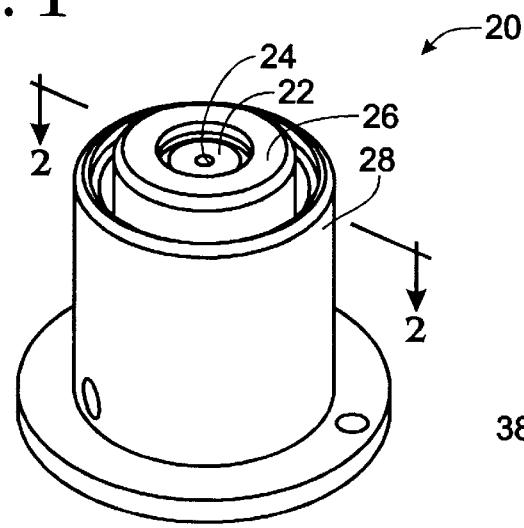
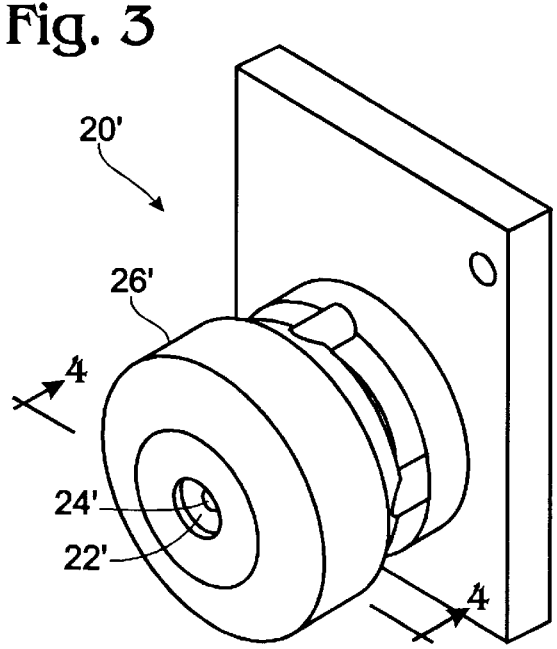
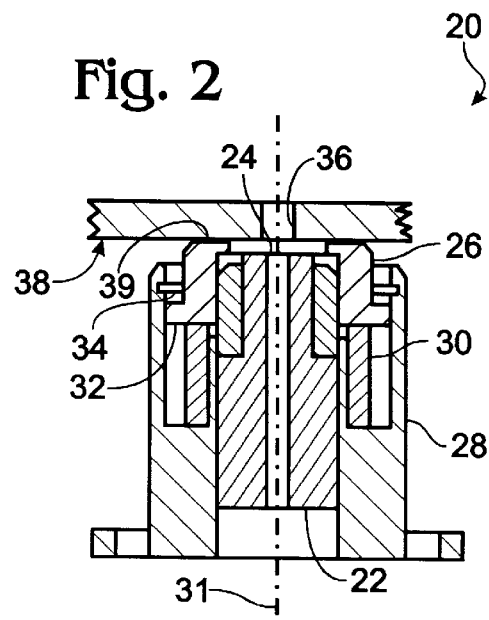
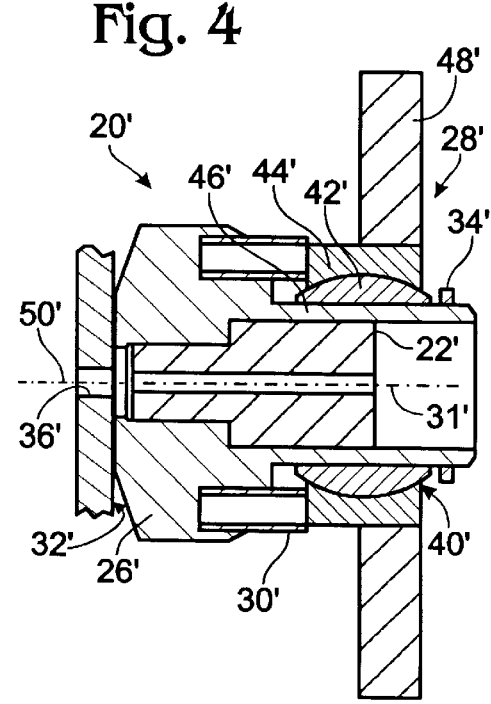

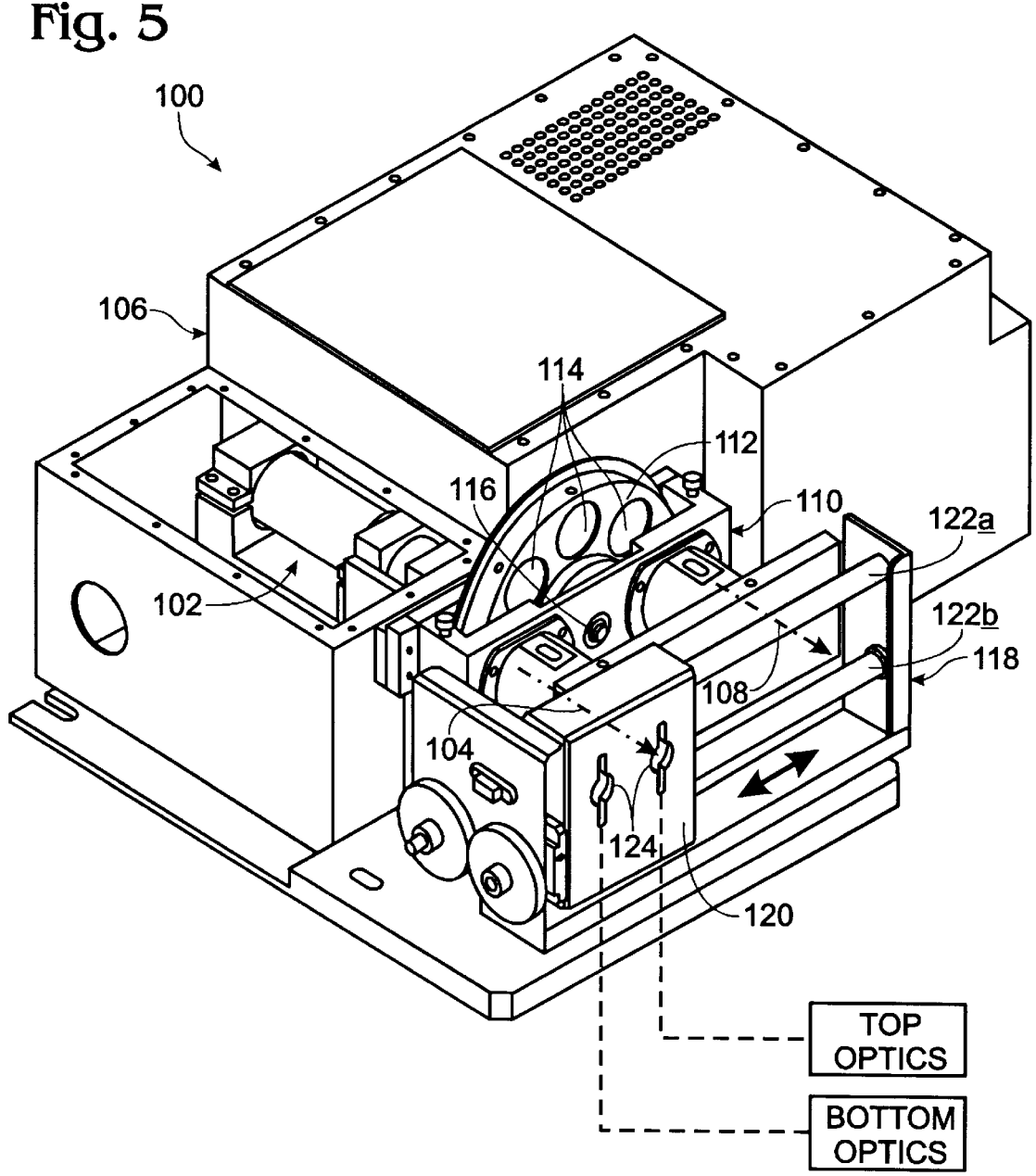

FLOATING HEAD ASSEMBLY

CROSS-REFERENCE TO RELATED APPLICATION

This application is a continuation of the following patent applications, each of which is incorporated herein by reference: U.S. patent application Ser. No. 09/062,472, filed Apr. 17, 1998; and PCT patent application Ser. No. PCT/US98/14575, filed Jul. 15, 1998.

This application is based upon and claims benefit under 35 U.S.C. §119 of the following U.S. Provisional Patent Applications, each of which is incorporated herein by reference: Ser. No. 60/052,876, filed Jul. 16, 1997; Ser. No. 60/059,639, filed Sep. 20, 1997; Ser. No. 60/063,811, filed Oct. 31, 1997; Ser. No. 60/072,499, filed Jan. 26, 1998; Ser. No. 60/072,780, filed Jan. 27, 1998; Ser. No. 60/075,414, filed Feb. 20, 1998; Ser. No. 60/075,806, filed Feb. 24, 1998; Ser. No. 60/082,253, filed Apr. 17, 1998; Ser. No. 60/084,167, filed May 4, 1998; Ser. No. 60/085,335, filed May 13, 1998; Ser. No. 60/085,500, filed May 14, 1998; and Ser. No. 60,089,848, filed Jun. 19, 1998.

This application incorporates by reference the following U.S. patent applications: Ser. No. 09/118,341 filed Jul. 16, 1998, and Ser. No. 09/118,141 filed Jul. 16, 1998.

FIELD OF THE INVENTION

This invention relates to devices and methods for transmitting light. More particularly, this invention relates to devices and methods for transmitting light through an aperture in a surface substantially without leakage.

BACKGROUND OF THE INVENTION

Optical systems typically include many components, which interact to generate, transmit, modify, and detect light. These components often are modular, permitting them to be combined in different ways for different applications. This modularity enhances flexibility but may diminish efficiency. In particular, gaps between modular components may permit stray (e.g., room) light to enter the optical system, lowering the signal-to-background ratio. Such gaps also may permit signal light to exit the system, lowering the signal.

Stray light has been reduced mostly by reducing the amount of ambient light available to enter the system. In some cases, stray light has been reduced by placing the entire optical system in a light-tight room, which is darkened when the optical system is in use. Unfortunately, this approach has a variety of shortcomings. It requires a dedicated room, which wastes space. It also requires the operator of the optical system to work in the dark, which is inherently unsafe, because the operator may have difficulty seeing the equipment, and because the operator may become drowsy. In other cases, stray light has been reduced by placing all or part of the optical system in a light-tight container. Unfortunately, this approach also has a variety of shortcomings. It hinders access to the components. It also reduces flexibility, because components must be chosen and arranged to fit within the container.

Signal light has been retained mostly by precisely aligning the optical system. Unfortunately, this approach also has a variety of shortcomings. In particular, it works best when optical components are fixed in position. It works less well when optical components are subject to vibration or when optical components must be moved during operation, such as in switching among plural light sources, detectors, and optical paths.

SUMMARY OF THE INVENTION

The present invention addresses these and other shortcomings by providing devices and methods for transmitting light through an aperture in a surface substantially without leakage, so that less stray light is introduced into optical systems and less signal light is lost.

In one embodiment, the device includes (1) an optical relay structure having an end configured to transmit light, and (2) an opaque collar positioned around the end and configured to reorient to conform to the surface when the end and the aperture are aligned, so that a substantially light-tight junction is formed. In this embodiment, the opaque collar further may be spring-biased relative to the end, so that the opaque collar is forced against the surface when the end and the aperture are aligned.

In another embodiment, the device includes (1) an optical relay structure having an end configured to transmit light, and (2) an opaque collar positioned around the end and spring-biased relative to the end, so that the opaque collar is forced against the surface when the end and the aperture are aligned, so that a substantially light-tight junction is formed. In this embodiment, the opaque collar may be configured to reorient to conform to the surface when the end and the aperture are aligned.

Preferred embodiments further may include a stop mechanism for limiting movement of the opaque collar, a registration mechanism for aligning the end and the aperture, and a light source and/or a detector for generating or detecting light, among others.

The invention also provides methods for forming and maintaining substantially light-tight junctions.

The nature of the invention will be understood more readily after consideration of the drawings and the detailed description of the invention that follow.

BRIEF DESCRIPTION OF THE FIGURES

FIG. 1 is a perspective view of a floating head assembly constructed in accordance with the invention.

FIG. 2 is a cross-sectional view of the floating head assembly, taken generally along the line 2—2 in FIG. 1.

FIG. 3 is a perspective view of an alternative floating head assembly.

FIG. 4 is a cross-sectional view of the alternative floating head assembly, taken generally along the line 4—4 in FIG. 3.

FIG. 5 is a partial perspective, partial schematic view of a light sensor module employed in conjunction with the invention.

DETAILED DESCRIPTION OF THE INVENTION

Floating Head Assemblies

Figure 6:
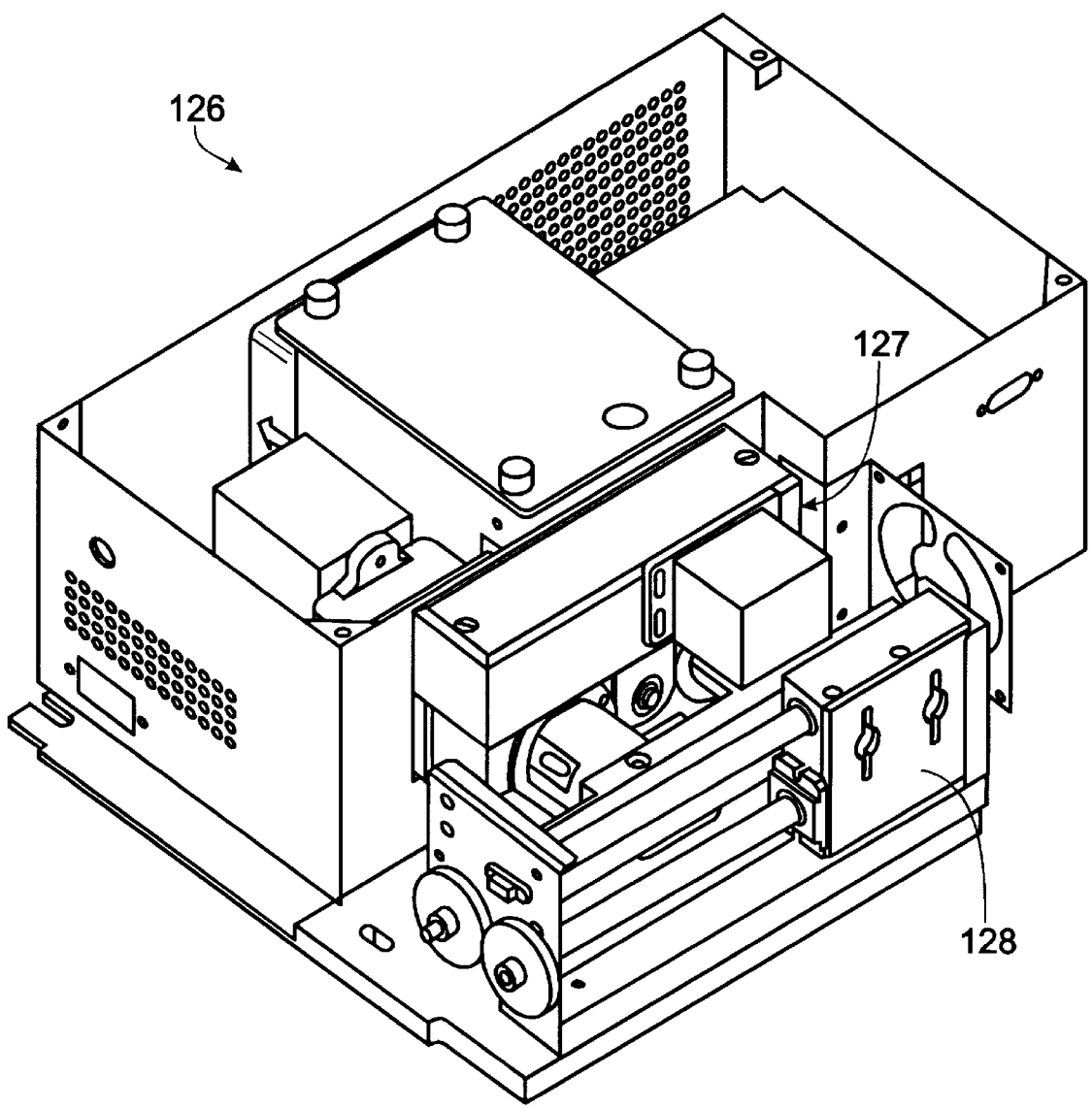
FIG. 6 is a partial perspective view of an alternative light sensor module.

FIG. 1 shows a perspective view of a floating head assembly 20 constructed in accordance with the invention.

Generally, floating head assembly 20 includes an optical relay structure 22 having an end 24 configured to transmit light, and an opaque collar 26 positioned around the end. Optical relay structure 22 is used to transmit light. Optical relay structure 22 preferably includes a fiber optic cable but also may include a light source, detector, or other optical component. Opaque collar 26 is used to block light and preferably comprises a hard plastic material. Opaque collar 26 encompasses and extends beyond end 24. An opaque base structure 28 contains additional elements. Together, opaque collar 26 and base structure 28 form a pair of concentric, partially overlapping walls positioned around optical relay structure 22.

FIG. 2 is a cross-sectional view of floating head assembly 20. A spring 30 is positioned between portions of opaque collar 26 and base structure 28. Spring 30 generally comprises any elastic body or other device that recovers its original shape when released after being distorted. Spring 30 is configured to spring-bias opaque collar 26 relative to end 24 when spring 30 is compressed between opaque collar 26 and base structure 28. Spring 30 bias pushes opaque collar 26 and base structure 28 in opposite directions parallel to a central axis 31 running through optical relay structure 22. A flange 32 on opaque collar 26 contacts a retaining ring 34 on base structure 28 when opaque collar 26 is maximally extended, limiting relative movement of opaque collar 26 and base structure 28. Additional or alternative stop mechanisms also may be employed, such as a set screw.

In use, floating head assembly 20 is positioned such that optical relay structure 22 is aligned with an aperture 36 in a surface 38, so that light may be transmitted between optical relay structure 22 and aperture 36. When end 24 and aperture 36 are aligned, a leading rim edge 39 of opaque collar 26 is spring-biased or forced against surface 38 by compression of spring 30. Leading rim edge 39 defines an end plane that is moveable relative to central axis 31. Opaque collar 26 and thus leading rim edge 39 automatically float or reorient relative to surface 38, forming a substantially light-tight junction by changing angle relative to central axis 31. This substantially light-tight junction substantially prevents stray light from entering the system, and it substantially prevents signal light from exiting the system. Spring 30 is relatively more compressed where surface 38 is closer to floating head assembly 20 and relatively less compressed where surface 38 is farther from floating head assembly 20, so that contact between opaque collar 26 and surface 38 is maintained for different positions and/or orientations of surface 38. Portions of opaque collar 26 may be formed of a material that deforms under pressure from spring 30 to conform substantially to asperities or other irregularities in surface 38.

FIG. 3 shows a perspective view of an alternative floating head assembly 20'. Generally, alternative floating head assembly 20' includes an optical relay structure 22' having an end 24' configured to transmit light, and an opaque collar 26' positioned around the end.

FIG. 4 shows a cross-sectional view of alternative floating head assembly 20'. Optical relay structure 22' and opaque collar 26' are supported by a base structure 28' that includes a spherical bearing 40' having an inner race 42' and an outer race 44'. Inner race 42' is slidingly connected to a sleeve portion 46' of opaque collar 26' that extends along optical relay structure 22'. Outer race 44' is connected to a platform structure 48 used for mounting alternative floating head assembly 20'. A spring 30' is positioned between portions of opaque collar 26' and outer race 44'. Spring 30' bias pushes opaque collar 26' and base structure 28' in opposite directions parallel to a central axis 31' running through optical relay structure 22'. A retaining ring 34' prevents overextension of opaque collar 26'.

In use, alternative floating head assembly 20' is positioned, like floating head assembly 20, such that optical relay structure 22' is aligned with an aperture 36 in a surface 38', so that light may be transmitted between optical relay structure 22' and aperture 36'. When so aligned, opaque collar 26' and optical relay structure 22' are free to compress and extend due to the action of spring 30', and to swivel and reorient due to the action of spherical bearing 40', relative to surface 38'. The combined actions of spring 30' and spherical bearing 40' ensure that central axis 31' of optical relay structure 22' always is substantially parallel to an aperture axis 50' running through aperture 36', unlike with floating head assembly 20.

Light Source and Detector Modules

FIG. 5 is a perspective view of a light source module 100 that employs floating head assemblies constructed in accordance with the invention. Portions of the module case have been removed to reveal internal componentry. Light source module 100 includes at least two light sources. A flashlamp 102 transmits light along a first light path 104. A second light source, namely, a continuous arc lamp (not shown) housed in compartment 106, transmits light along a second light path 108. A filter wheel assembly 110 is positioned adjacent the light sources. Filter wheel assembly 110 includes a filter wheel 112, which holds a plurality of filters 114. Filter wheel 112 is rotatable around an axis 116, so that a given filter can be positioned interchangeably along light path 104, or along light path 108, by rotating filter wheel 112. A fiber optic shuttle assembly 118 is mounted next to filter wheel assembly 110. Moveable shuttle 120 translates along support tracks 122a and 122b, so that moveable shuttle 120 can be positioned in front of a selected light source for a selected assay application. Two fiber optic ports 124 are provided on an external face of shuttle 120. Fiber optic ports 124 direct light, via fiber optic cables, from a selected source either to a top optics head or to a bottom optics head, above and below a stage holding a sample, respectively.

FIG. 6 is a perspective view of an alternative light source module 126. In this embodiment, filter wheel assembly 110 of light source module 100 has been replaced by an alternative filter wheel assembly 127. A moveable shuttle 128 is shown in an alternative position relative to moveable shuttle 120 in light source module 100.

Figure 7:
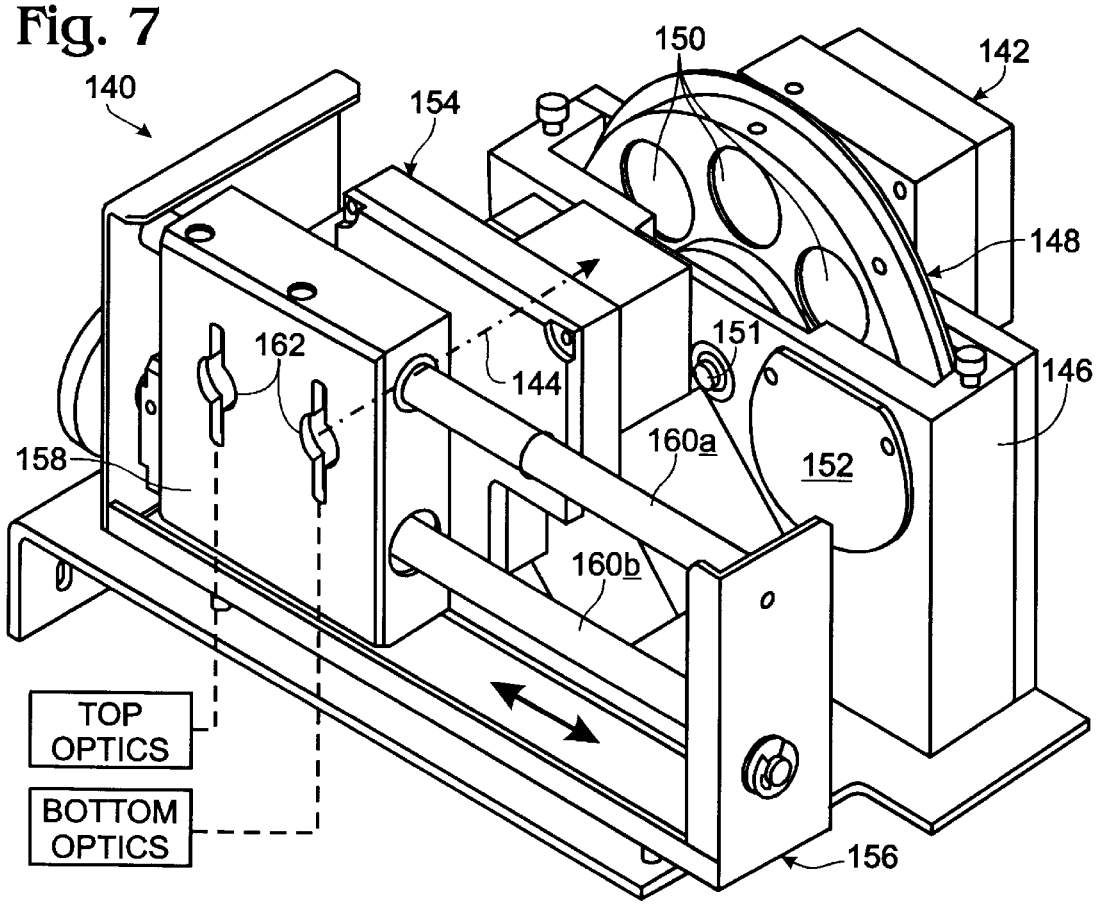
FIG. 7 is a partial perspective, partial schematic view of a detector module employed in conjunction with the invention.

FIG. 7 is a perspective view of a detector module 140 that employs floating head assemblies constructed in accordance with the invention. Portions of the module case have been removed to reveal internal componentry. Detector module 140 is similar to light source module 100. A detector 142 receives light directed along a light path 144, originating from a sample. A filter wheel assembly 146 is positioned in front of detector 142. Filter wheel assembly 146 includes a plurality of filters 150 and is rotatable around an axis 151 by a stepper, DC servo, or other motor. The filter wheel can be rotated at a preselected angular speed to allow synchronization with a flash lamp light source and a detector. A port 152 for a second detector is provided in filter wheel assembly 146, so that a second detector can be mounted in detector module 140. A given filter in filter wheel 148 can be positioned along a first light path 144 leading to detector 142, or alternatively can be positioned along a second light path leading to a second detector (not shown). An attenuator mechanism 154 is mounted adjacent filter wheel assembly 146. A fiber optic shuttle assembly 156 is mounted in front of attenuator mechanism 154. Shuttle assembly 156 includes a moveable shuttle 158, which is moveable along upper and lower support tracks 160*a* and 160*b*, respectively. An exterior face of shuttle 158 has two fiber optic ports 162, one of which is connected, via a fiber optic cable, to a top optics head above the examination site, the other of which is connected, via a fiber optic cable, to a bottom optics head below the examination site. In operation, moveable shuttle 158 can be moved along support tracks 160*a* and 160*b* to connect optically either one of the optics heads to any one of the detectors (if more than one is included in the module), and through any one of filters 150 in filter wheel 148.

Figure 8:
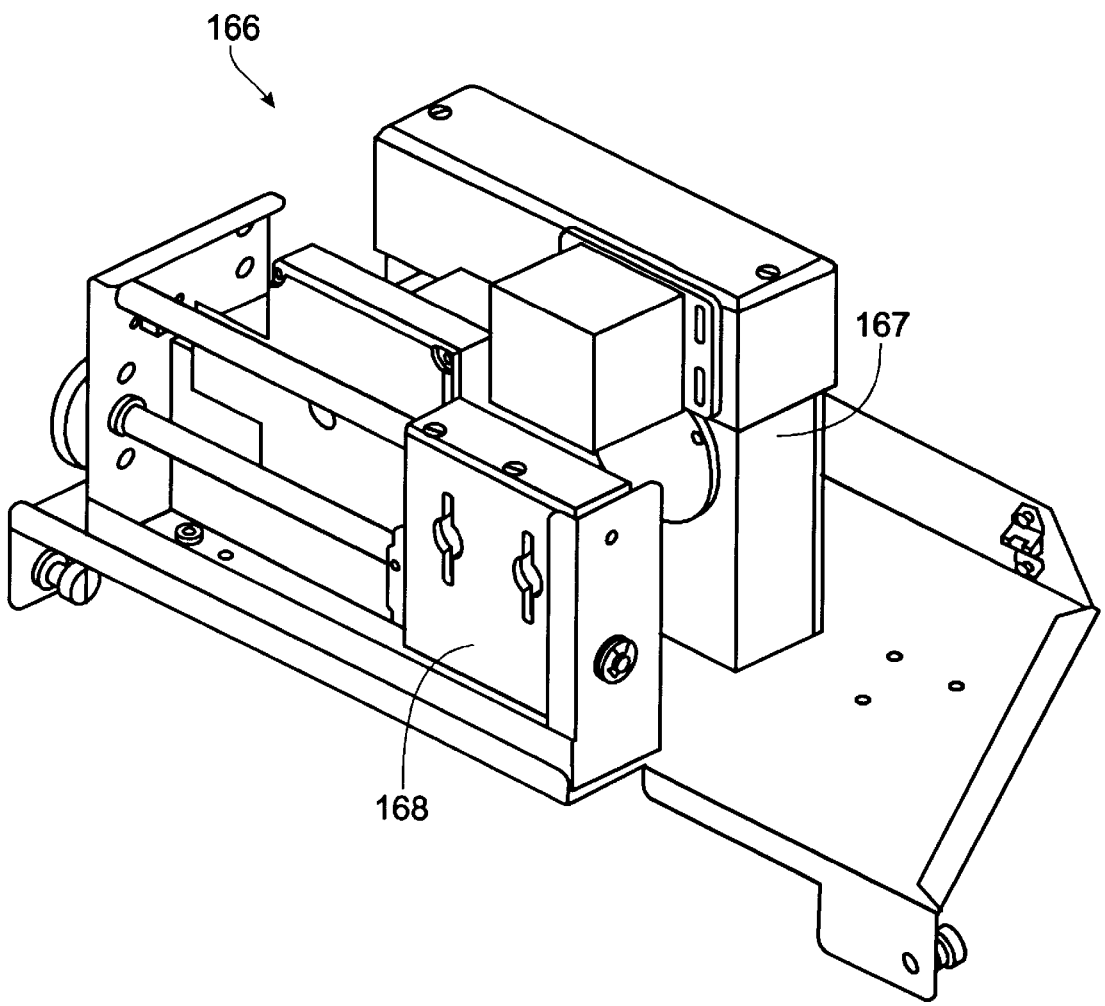
FIG. 8 is a partial perspective view of an alternative detector module.

FIG. 8 is a perspective view of an alternative detector module 166. In this embodiment, filter wheel assembly 146 of detector module 140 has been replaced by an alternative filter wheel assembly 167. A moveable shuttle 168 is shown in an alternative position relative to moveable shuttle 158 in detector module 140.

Light source and detector modules are designed for flexibility. Additional ports for fiber optics or other optical relay structures may be provided, if desired. The number and configuration of such other ports may be tied to the number and configuration of light-transmission routes through the filter wheel. Optical components also may be connected directly to the moveable shuttle. Such a connection would be especially useful for small, dedicated components, such as a beamsplitter and photodiode-type detector that could sample a portion of the light transmitted through the port to correct for output fluctuations from a light source.

A comparison of FIGS. 5 and 7, and FIGS. 6 and 8, shows that many aspects of light source modules 100 and 126 and detector modules 140 and 166 are the same, particularly the mechanics of filter wheel assemblies 110 and 146, filter wheel assemblies 127 and 167, and fiber optic shuttle assemblies 118 and 156. The light source and detector modules both function as registration mechanisms that align the end of an optical relay structure with an aperture in a surface. This surface may enclose a light source, detector, or other optical component. The light source and detector modules both permit alignment with two such apertures, and with portions of a surface not including an aperture to prevent the optical relay structure from transmitting light. Light source and detector modules also may be configured to transmit light directly from module to module, using air, a tube, or other mechanism to transmit light. If used together in a light detection device, the light source and detector modules provide a great deal of analytical flexibility to select different combinations of light sources, detectors, and filters for different applications, while also being able to select different combinations of top versus bottom illumination and detection orientations.

Figure 9:
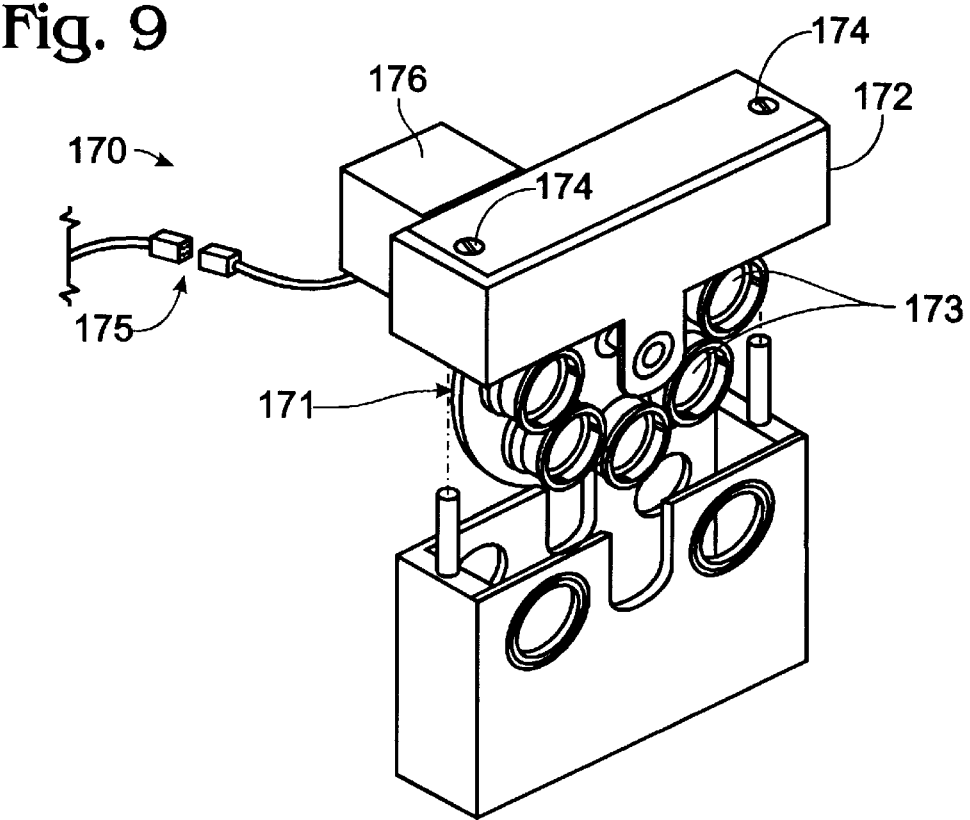
FIG. 9 is a partially exploded perspective view of a filter wheel assembly employed in conjunction with the invention.

FIG. 9 is a partially exploded perspective view of a filter wheel assembly 170 like those used in light source module 126 and detector module 166. Filter wheel assembly 170 functions generally like filter wheel assemblies 110, 146 used in light source module 100 and detector module 140, as described above. However, in filter wheel assembly 170, the filter wheel 171 is connected to a top 172 that easily may be removed to permit access to the filters 173. Top 172 is removed by loosening two captive screws 174 on top 172 and unplugging an electrical connector 175 attached to a driver 176 for filter wheel 171. Top 172 is reinstalled by reversing the procedure.

Figure 10:
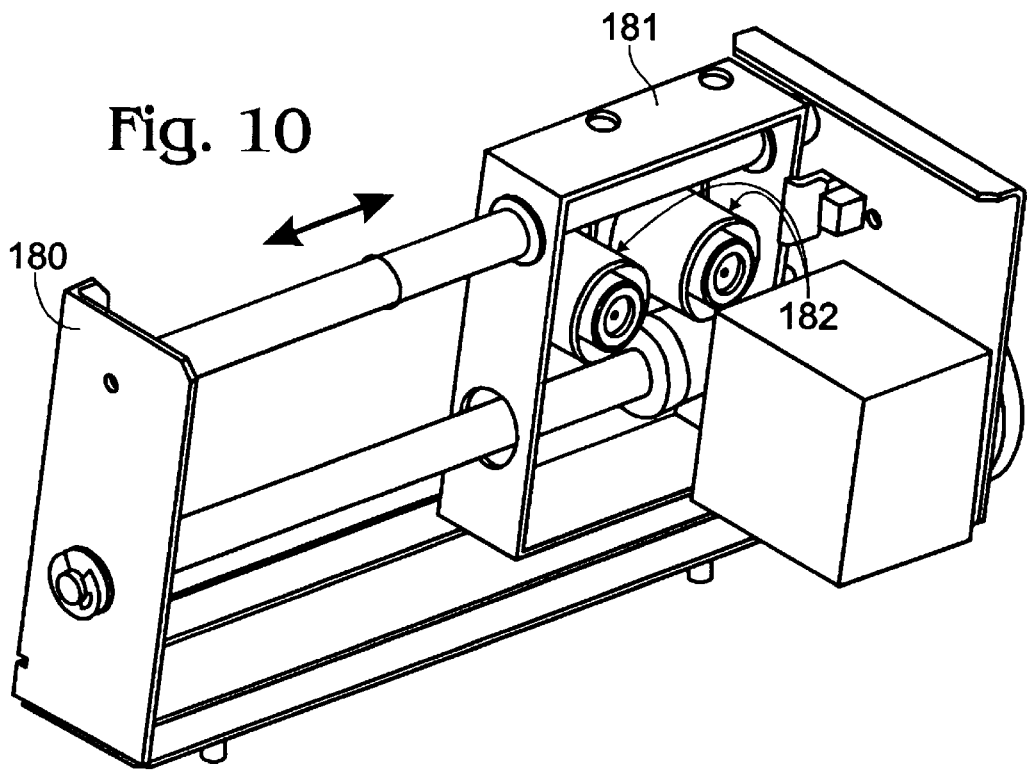
FIG. 10 is a partial perspective view of a fiber optic shuttle assembly employed in conjunction with the invention.

FIG. 10 is a partial perspective view of a fiber optic shuttle assembly 180 like those used in light source module 100 and detector module 140. Fiber optic shuttle assembly 180 includes a moveable shuttle 181 and two floating head assemblies 182. Among other applications, each floating head assembly 182 may be used to create and maintain a light-tight connection between selected light sources or detectors and fiber optic cables, such as those that lead to an examination site, or to a top optics head or a bottom optics head, above and below a stage, respectively.

Methods

The invention also provides methods for forming and maintaining substantially light-tight junctions.

In one embodiment, the method includes (1) providing first and second light fixtures housed in first and second light fixture slots, each light fixture slot having an aperture for transmitting light, wherein the apertures are located on a common surface; (2) providing a device for transmitting light through the aperture, the device including an optical relay structure having an end configured to transmit light, and an opaque collar positioned around the end; (3) aligning the device with one of the apertures; (4) forming a substantially light-tight junction by reorienting the opaque collar to conform to the surface; and (5) aligning the device with the other of the apertures by translating the device so that the opaque collar maintains substantially light-tight contact with the common surface.

In another embodiment, the above method is modified by replacing step (4) comprising "forming a substantially light-tight junction by reorienting the opaque collar to conform to the surface" with another step (4) comprising "forming a substantially light-tight junction by spring-biasing the opaque collar relative to the end, so that the opaque collar is forced against the surface."

Accordingly, while the invention has been disclosed in preferred forms, the specific embodiments thereof as disclosed and illustrated herein are not to be considered in a limiting sense, because numerous variations are possible and no single feature, function, or property of the preferred embodiments are essential. The invention is to be defined only by the scope of the issued claims.

We claim:

1. A device for transmitting light through an aperture in a surface, the device comprising:
   an optical relay structure having an end configured to transmit light;
   an operative mounting mechanism that permits relative motion between the optical relay structure and the surface in a direction substantially parallel to a tangent to the surface, so that the end and the aperture may be brought into and out of alignment; and
   an opaque collar positioned around the end and configured to reorient to conform to the surface when the end and the aperture are aligned, so that a substantially light-tight junction is formed.

2. The device of claim 1, wherein the optical relay structure includes a central axis the opaque collar reorienting by changing angle relative to the central axis.

3. The device of claim 1, wherein the opaque collar is spring-biased relative to the end, so that the opaque collar is forced against the surface when the end and the aperture are aligned.

4. The device of claim 1, further comprising:
   a base;
   a spring operatively associated with the base, wherein the opaque collar is spring-biased relative to the end when the spring is compressed between the opaque collar and the base; and
   a stop mechanism configured to limit relative movement of the opaque collar and the base.

5. The device of claim 1, wherein the optical relay structure includes at least one of a fiber optic cable, a light source, and a detector.

6. The device of claim 1, wherein the surface is substantially flat.

7. The device of claim 1, further comprising a registration mechanism configured to align the end and the aperture.

8. The device of claim 7, wherein the surface includes two apertures, and the registration mechanism is capable of aligning the end with either aperture.

9. The device of claim 7, wherein the registration mechanism is capable of aligning the end with a portion of the surface not including an aperture to prevent the optical relay structure from transmitting light.

10. The device of claim 1, further comprising a spring, wherein at least a portion of the opaque collar deforms under pressure from the spring substantially to conform to asperities in the surface.

11. The device of claim 1, further comprising a light source positioned on a side of the surface opposite the optical relay structure, so that when the end of the optical relay structure is aligned with the aperture, light from the light source can be transmitted through the aperture and optical relay structure substantially without leakage.

12. The device of claim 1, further comprising a detector positioned on a side of the surface opposite the optical relay structure, so that when the end of the optical relay structure is aligned with the aperture, light can be transmitted through the optical relay structure and aperture to the detector substantially without leakage.

13. A device for transmitting light through an aperture in a surface, the device comprising:

an optical relay structure having an end configured to transmit light; and an opaque collar positioned around the end and spring-biased relative to the end, so that the opaque collar is forced against the surface when the end and the aperture are aligned, so that a substantially light-tight junction is formed.

14. The device of claim 13, wherein the opaque collar is configured to reorient to conform to the surface when the end and the aperture are aligned.

15. The device of claim 13, further comprising:

a base;

a spring operatively associated with the base, wherein the opaque collar is spring-biased relative to the end when the spring is compressed between the opaque collar and the base; and a stop mechanism configured to limit relative movement of the opaque collar and the base.

16. The device of claim 13, wherein the optical relay structure includes at least one of a fiber optic cable, a light source, and a detector.

17. The device of claim 13, wherein the surface is substantially flat.

18. The device of claim 13, further comprising a registration mechanism configured to align the end and the aperture.

19. The device of claim 18, wherein the surface includes two apertures, and the registration mechanism is capable of aligning the end with either aperture.

20. The device of claim 18, wherein the registration mechanism is capable of aligning the end with a portion of the surface not including an aperture to prevent the optical relay structure from transmitting light.

21. The device of claim 13, wherein at least a portion of the opaque collar deforms under pressure from the spring substantially to conform to asperities in the surface.

22. The device of claim 13, further comprising a light source positioned on a side of the surface opposite the optical relay structure, so that when the end of the optical relay structure is aligned with the aperture, light from the light source can be transmitted through the aperture and optical relay structure substantially without leakage.

23. The device of claim 13, further comprising a detector positioned on a side of the surface opposite the optical relay structure, so that when the end of the optical relay structure is aligned with the aperture, light can be transmitted through the optical relay structure and aperture to the detector substantially without leakage.

24. A device for transmitting light through an aperture in a surface, the device comprising:

an optical relay structure having a central axis and an end configured to transmit light;

first and second opaque walls positioned around the end, the opaque walls being concentric and partially overlapping; and a biasing mechanism to force the opaque walls in opposite directions parallel to the central axis, so that the first opaque wall is spring-biased against the surface to form a substantially light-tight junction when the end and the aperture are aligned.

25. The device of claim 24, wherein one of the opaque walls has a flange that limits relative movement of the walls.

26. A method of light-tight switching between two light fixtures, the method comprising:

providing first and second light fixtures housed in first and second light fixture slots, each light fixture slot having an aperture for transmitting light, wherein the apertures are located on a common surface;

providing a device for transmitting light through the aperture, the device including (1) an optical relay structure having an end configured to transmit light, and (2) an opaque collar positioned around the end;

aligning the device with one of the apertures;

forming a substantially light-tight junction by reorienting the opaque collar to conform to the surface; and aligning the device with the other of the apertures by translating the device so that the opaque collar maintains substantially light-tight contact with the common surface.

27. The method of claim 26, wherein the two light fixtures are light sources.

28. The method of claim 26, wherein the two light fixtures are detectors.

29. A method of light-tight switching between two light fixtures, the method comprising:

providing first and second light fixtures housed in first and second light fixture slots, each light fixture slot having an aperture for transmitting light, wherein the apertures are located on a common surface;

providing a device for transmitting light through the aperture, the device including (1) an optical relay structure having an end configured to transmit light and (2) an opaque collar positioned around the end;

aligning the device with one of the apertures;

forming a substantially light-tight junction by spring-biasing the opaque collar relative to the end, so that the opaque collar is forced against the surface; and aligning the device with the other of the apertures by translating the device so that the opaque collar maintains substantially light-tight contact with the common surface.

30. The device of claim 1, the aperture having an aperture axis, the optical relay structure having a central axis, wherein the central axis remains substantially parallel to the aperture axis as the end and the aperture are aligned.

31. The device of claim 13, further comprising an operative mounting mechanism that permits relative motion between the optical relay structure and the surface in a direction substantially parallel to a tangent to the surface, so that the end and the aperture may be brought into and out of alignment.

32. The device of claim 13, the aperture having an aperture axis, the optical relay structure having a central axis, wherein the central axis remains substantially parallel to the aperture axis as the end and the aperture are aligned.

33. A device for transmitting light through an aperture in a surface, the device comprising:
- an optical relay structure having an end configured to transmit light;
- an opaque collar positioned around the end and configured to reorient to conform to the surface when the end and the aperture are aligned, so that a substantially light-tight junction is formed;
- a base;
- a spring operatively associated with the base, wherein the opaque collar is spring-biased relative to the end when the spring is compressed between the opaque collar and the base; and
- a stop mechanism configured to limit relative movement of the opaque collar and the base.

34. A device for transmitting light through an aperture in a surface, the device comprising:
- an optical relay structure having an end configured to transmit light;
- an opaque collar positioned around the end and configured to reorient to conform to the surface when the end and the aperture are aligned, so that a substantially light-tight junction is formed; and
- a registration mechanism configured to align the end and the aperture, wherein the registration mechanism is capable of aligning the end with a portion of the surface not including an aperture to prevent the optical relay structure from transmitting light.

35. The device of claim 34, wherein the surface includes two apertures, and the registration mechanism is capable of aligning the end with either aperture.

36. The device of claim 34, wherein the opaque collar is spring-based relative to the end, so that the opaque collar is forced against the surface when the end and the aperture are aligned.

37. A device for transmitting light through an aperture in a surface, the device comprising:
- an optical relay structure having an end configured to transmit light;
- an opaque collar positioned around the end and configured to reorient to conform to the surface when the end and the aperture are aligned, so that a substantially light-tight junction is formed; and
- a spring;
- wherein at least a portion of the opaque collar deforms under pressure from the spring substantially to conform to asperities in the surface.

38. A device for transmitting light through an aperture in a surface, the device comprising:
- an optical relay structure having a central axis and an end configured to transmit light; and
- an opaque collar positioned around the end and configured to reorient to conform to the surface when the end and the aperture are aligned, so that a substantially light-tight junction is formed;
- wherein the central axis of the optical relay structure remains substantially parallel to an aperture axis of the aperture as the end and the aperture are aligned.

39. The device of claim 38, wherein the opaque collar is spring-based relative to the end, so that the opaque collar is forced against the surface when the end and the aperture are aligned.

40. A device for transmitting light through an aperture in a surface having two apertures, the device comprising:
- an optical relay structure having an end configured to transmit light;
- an opaque collar positioned around the end and configured to reorient to conform to the surface when the end and one of the two apertures are aligned, so that a substantially light-tight junction is formed; and
- a registration mechanism configured to align the end and the aperture, wherein the registration mechanism is capable of aligning the end with either aperture.

41. The device of claim 40, wherein the registration mechanism is capable of aligning the end with a portion of the surface not including an aperture to prevent the optical relay structure from transmitting light.

42. The device of claim 40, wherein the opaque collar is spring-biased relative to the end, so that the opaque collar is forced against the surface when the end and the aperture are aligned.

* * * * *

UNITED STATES PATENT AND TRADEMARK OFFICE
CERTIFICATE OF CORRECTION

PATENT NO. : 6,033,100
DATED : March 7, 2000
INVENTOR(S) : Samuel A. Marquiss et al.

It is certified that error appears in the above-identified patent and that said Letters Patent is hereby corrected as shown below:

Column 9,
Line 7, delete "and" and insert -- or -- therefor.
Line 47, delete "based" and insert -- biased -- therefor.

Column 10,
Line 26, delete "based" and insert -- biased -- therefor.

Signed and Sealed this

Second Day of April, 2002

*Attest:*

JAMES E. ROGAN
*Attesting Officer*       *Director of the United States Patent and Trademark Office*